US008294081B2

(12) United States Patent
Rosenheimer et al.

(10) Patent No.: US 8,294,081 B2
(45) Date of Patent: Oct. 23, 2012

(54) SURGICAL LAMPS AND METHODS OF ILLUMINATING A SURGICAL SITE

(75) Inventors: Rouven Rosenheimer, München (DE); Willibald Hiemer, Munich (DE); Martin Schenk, Gomaringen (DE)

(73) Assignee: Trumpf Medizin Systeme GmbH + Co. KG, Saalfeld (DE)

(*) Notice: Subject to any disclaimer, the term of this patent is extended or adjusted under 35 U.S.C. 154(b) by 397 days.

(21) Appl. No.: 12/269,478

(22) Filed: Nov. 12, 2008

(65) Prior Publication Data

US 2009/0127433 A1 May 21, 2009

(30) Foreign Application Priority Data

Nov. 13, 2007 (EP) .................................... 07022009

(51) Int. Cl.

*G02F 1/01* (2006.01)
*G01J 3/50* (2006.01)
*H01L 27/00* (2006.01)

(52) U.S. Cl. ...................... 250/225; 250/226; 250/208.1

(58) Field of Classification Search .................. 250/205, 250/225, 216, 559.04, 559.05, 559.07, 559.08, 250/559.09, 559.39, 208.1, 458.1, 462.1, 250/208.12, 226; 359/483, 386, 484; 372/27; 362/804, 572, 19

See application file for complete search history.

(56) References Cited

U.S. PATENT DOCUMENTS 2,423,321 A 7/1947 Hurley, Jr.
4,678,900 A * 7/1987 Nishioka ....................... 250/205
4,759,615 A 7/1988 Bainbridge et al.
5,450,857 A * 9/1995 Garfield et al. ............... 600/591
6,028,303 A 2/2000 Suzuki
2001/0024277 A1* 9/2001 Hirosawa et al. ............ 356/369
2002/0088927 A1 7/2002 Simchoni
2004/0227989 A1 11/2004 Obrebski et al.
2006/0241495 A1* 10/2006 Kurtz ........................... 600/476

FOREIGN PATENT DOCUMENTS

CA 2 617 262 2/2007
DE 68 08 513 U 11/1968
DE 3435369 * 5/1985
WO WO 96/17206 6/1996
WO WO 2007/014629 2/2007

OTHER PUBLICATIONS

European Search Report from corresponding European Patent Application No. 07 02 2009, mailed Mar. 6, 2008, with English translation of pp. 2 and 3, 6 pages total.

English translation of Summons to Oral Proceedings from corresponding European Patent Application No. 07022009.0, mailed Oct. 19, 2011, 5 pages.

* cited by examiner

*Primary Examiner* — Que T Le
*Assistant Examiner* — Pascal M. Bui-Pho
(74) *Attorney, Agent, or Firm* — Fish & Richardson P.C.

(57) ABSTRACT

A surgical lamp includes a light source, a camera, at least one rotatable polarization filter, and a control device that controls the polarization filter according to the results of an evaluation of the image which is captured by the camera.

17 Claims, 3 Drawing Sheets

Fig 2b

SURGICAL LAMPS AND METHODS OF ILLUMINATING A SURGICAL SITE

CROSS REFERENCE TO RELATED APPLICATION

This application claims priority under 35 U.S.C. §119(a) to European Application No. 07 022 009.0, filed on Nov. 13, 2007, the entire contents of which are hereby incorporated by reference.

TECHNICAL FIELD

This description relates to a surgical lamp and a method for illuminating a surgical site.

BACKGROUND

As to surgical lamps, priority is normally given to optimized illumination of the surgical site. Specific structures such as lymphatic vessels, tumors, metastases and applied stem cells, etc. often are not clearly delimitable from surrounding tissue. They are identified mainly by the anatomic knowledge and the experience of the surgeon. In some cases, they are not at all identifiable macroscopically.

SUMMARY

The target structure at the surgical site can be depicted in the shortest time and it can be delimitated from the surrounding tissue without the surgeon having to manipulate the surgical lamp. Therefore the surgeon is able to concentrate more on the surgery.

Existing surgical lamps can be upgraded to extend their field of application.

In one general aspect, a surgical lamp includes a light source, a camera, and at least a first polarization filter that is rotatable.

Implementations can include one or more of the following features. The surgical lamp can include at least a second polarization filter such that a polarizer and an analyzer are formed from, respectively, the at least second polarization filter and the at least first polarization filter. The second polarization filter can be rotatable.

The light source can emit narrowband light.

The surgical lamp can include a control unit configured to rotate the first polarization filter in accordance with the results of an evaluation of the image captured by the camera.

The surgical lamp can include a filter positioned in front of a light entrance of the camera and configured for letting through a defined wavelength range. The surgical lamp can include a mechatronic drive unit for rotating the first polarization filter. The surgical lamp can include an electronic evaluation unit connected to the camera and configured to evaluate the image brightness of the image captured by the camera. The electronic evaluation unit can be designed in a such way that it integrates the brightness in the whole region of the image. The electronic evaluation unit can be designed in a way that it determines the distribution of brightness in the whole region of the image. The surgical lamp can include a control unit coupled to the first polarization filter and to the electronic evaluation unit to rotate the first polarization filter in accordance with results of evaluation from the evaluation unit.

The first polarization filter can be placed between the camera and a surgical site.

The surgical lamp can include at least a second polarization filter that is placed between the light source and the surgical site.

In another general aspect, a surgical site is illuminated with a surgical lamp, which includes a light source, a camera, and at least one rotatable polarization filter. An image of the surgical site is captured with the at least one rotatable polarization filter and the camera. The captured image is evaluated, and one or more of the polarization filters are rotated based on the results of the evaluation of the image captured by the camera.

Implementations can include one or more of the following features. For example, the rotation can occur automatically. The surgical site can be illuminated with polarized light from the light source.

The surgical site can be illuminated with excitation light for fluorescence radiation. The excitation light can be narrowband.

The one or more of the polarization filters can be rotated by rotating the one or more polarization filters automatically until the total brightness of a viewed zone in the captured image drops below a threshold value. The one or more of the polarization filters can be rotated by rotating the one or more polarization filters until the area of the brighter illuminated zones in the captured image drops below a threshold value.

The surgical lamp can include a filter in front of an objective of the camera and being configured to let pass light within a wavelength range.

The image can be captured by placing the one or more polarization filter between the camera and the surgical site. Light from the light source can be directed through at least a second polarization filter that is placed between the light source and the surgical site.

In another general aspect, a surgical lamp includes a light source, a camera, at least one first polarization filter that is rotatable and placed between a surgical site and the camera to receive light from the light source that is reflected from the surgical site and light that is caused by fluorescence at the surgical site, an electronic evaluation unit connected to the camera and configured to evaluate the image brightness of the image captured by the camera and to compare the image brightness to a threshold value, and a control unit coupled to the at least one first polarization filter and configured to rotate the at least one first polarization filter to reduce the image brightness.

BRIEF DESCRIPTION OF THE DRAWINGS

FIG. 2*b* is a camera image of the surgical site of FIG. 2*a* in which the reflections are reduced.

DETAILED DESCRIPTION

Figure 1:
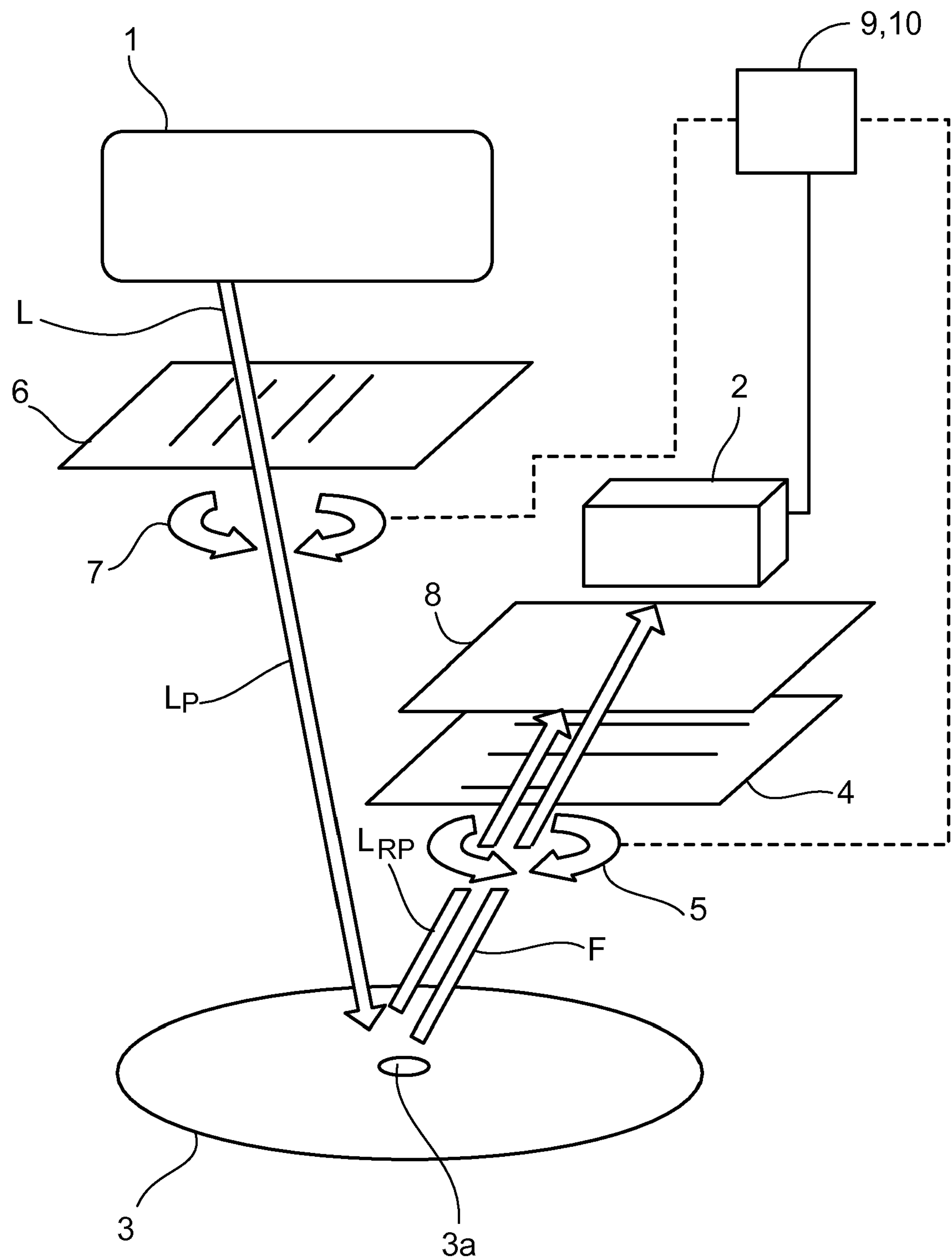
FIG. 1 is a diagrammatic illustration of a surgical lamp.

As can be seen in FIG. 1, the surgical lamp includes a light source 1 and a detector formed by a camera 2. The light source 1 includes, e.g., a source for white light and/or a source for narrowband light of certain wavelengths for stimulating a fluorophore at a surgical site 3. Narrowband light can be within a range of, for example, 40 nm, 20 nm, 10 nm, or 5 nm. For example, the light source 1 can include one or more light emitting diodes (LEDs). A blue LED can be used as a light source 1 for the fluorophore Fluorescein, which emits non-polarized light of 450±5 nm. The wavelength range of the light emitted by the light source therefore is 445 nm-455 nm when using a royal blue LED. Advantageously the wavelength range is chosen to be in the range where the fluorophore is sensitive. The light source may have any arbitrary shape. Particularly, a planar lightning may be realized by multiple LEDs. Typically, the light source is arranged above the surgical site 3.

The detector 2 can be formed as a CCD camera that captures an image of the surgical site 3. The camera can include an integrated image alignment unit and an autofocus.

In front of an objective of the detector 2, a first polarization filter 4 is arranged. The polarization filter 4 forms an analyzer in that it receives the image from the surgical site 3, and light emitted through the polarization filter 4 is analyzed by the detector 2 and an evaluation unit 9 connected to the camera 2. The polarization filter 4 is rotatable by a schematically illustrated drive unit 5. Between the light source 1 and the surgical site 3, a second polarization filter 6 is provided, and the second polarization filter 6 forms a polarizer in that is polarized the light from the light source 1. The second polarization filter 6 is rotatable by a schematically illustrated drive unit 7.

Further, a filter, e.g., an interference filter 8, is provided in front of the objective of the camera 2. The interference filter 8 transmits a certain wavelength range and blocks wavelengths that are not desired.

The camera 2, the filter 8, the polarization filter 4, and the drive unit 5 can be arranged in a housing. This housing may be provided separately besides the light source 1. In some implementations, this housing is integrated in the construction of the surgical light, e.g., amongst an arrangement of LEDs. The housing can be provided with a detachable handle that is sterilizable. In this way, the surgeon can adjust the surgical lamp to the desired position.

The camera 2 is connected to the evaluation unit 9, which may be formed, e.g. as an Erasable Programmable Logic Device (EPLD) with an upstream 8 bit analog digital converter. The evaluation unit 9 is connected to a monitor that shows the image of the surgical site 3 captured by the camera 2. Furthermore, the evaluation unit 9 is connected to a control unit 10 that controls the drives 5, 7 of the polarization filters 4, 6, respectively. The evaluation unit 9, the control unit 10, and the drives 5, 7 form a mechatronical system. The control unit 10 controls the mechatronical drives 5, 7 based on the evaluation results of the evaluation unit 9.

In use, non-polarized light L from the light source 1 is (partly) polarized by the second polarization filter 6 to produce (partly) polarized light $L_P$. The polarized light $L_P$ impinges on the surgical site 3. The surgical site 3 is prepared in a such way that specific structures 3*a* contain a fluorophore, e.g., Fluorescein. For example, the fluorophore can be applied to the tissue and it can be transported to the corresponding lymph node by draining lymph channels. The fluorophore is excited by the narrowband light (excitation light) emitted by the light source 1 to fluoresce and emits the (nonpolarized) fluorescent light F, which usually has a larger wavelength than the excitation light $L_P$. Hence, the excitation light $L_P$ is reflected in certain zones simultaneously and this reflected excitation light is labeled as $L_{RP}$. These zones in which the excitation light is reflected can be zones of tissue or faces of instruments.

The fluorescence light F and the reflected excitation light $L_{RP}$ impinge on the first polarization filter 4. The fluorescence light F is allowed to pass because it is nonpolarized. The reflected excitation light $L_{RP}$ is polarized and is allowed to pass fully, not at all, or partly, depending on the rotating position of the first polarization filter. After emerging from the first polarization filter 4, the fluorescence light F and the reflected excitation light $L_{RP}$ pass through the filter 8, which extinguishes light with a different wavelength than the wavelength range that is allowed to pass and that comes from, e.g., additional lighting by white light. The camera 2 generates an image of the surgical site 3.

Thereafter, the evaluation unit 9 evaluates online all of the pixels of the CCD matrix of the camera 2 using, for example, digital image processing. The evaluation is carried out with an algorithm, e.g., the determination of the minimum of the image brightness, the constitution of a sum integral, etc. According to some implementations of the evaluation, the image brightness is integrated over the viewed zone.

The image brightness changes by turning one or both polarization filters 4, 6. One or both polarization filters 4, 6 are turned with the mechatronic drive units 5 and 7, respectively, until the result of the evaluation is a minimum image brightness or an image brightness that drops below a maximum acceptable value. Thereby, the reduction of the image brightness is caused mainly by the extinction of the reflections of the excitation light.

Figure 2A:
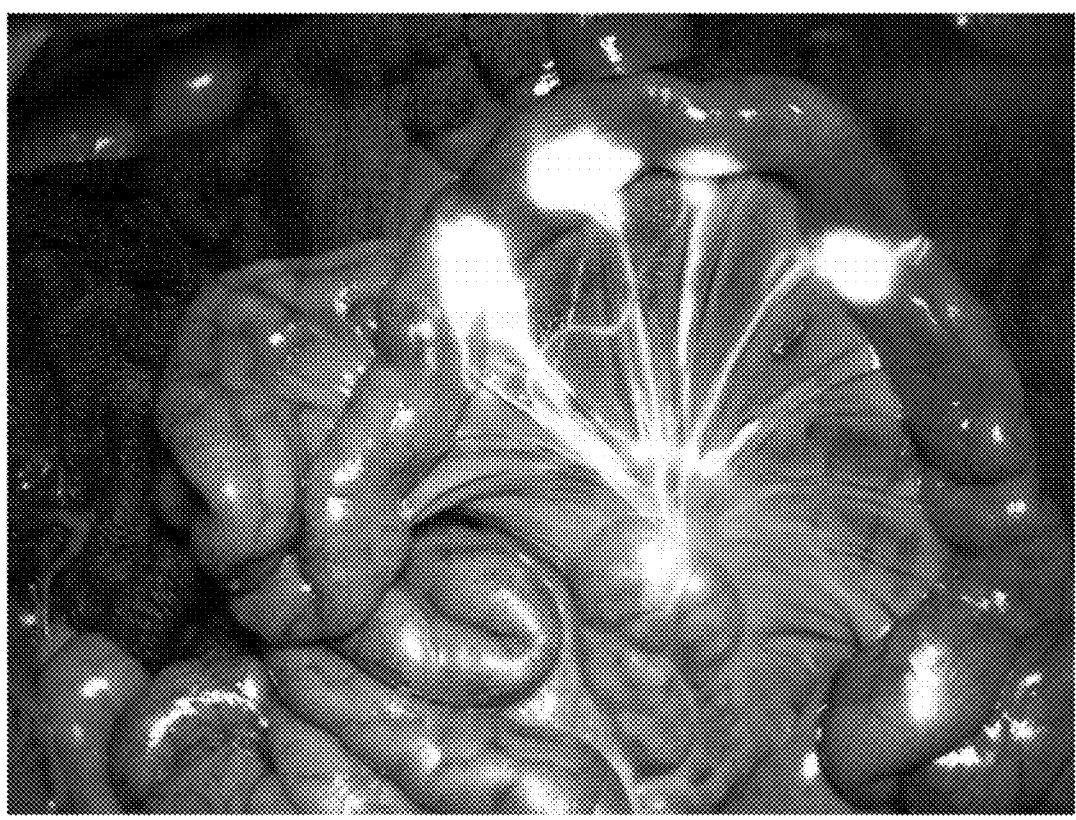
FIG. 2*a* is a camera image of a surgical site with fluorescent zones and reflective zones.

FIG. 2*a* illustrates a surgical site with fluorescent lymph channels and the corresponding lymph node as well as further bright zones showing the reflected excitation light.

Figure 2B:
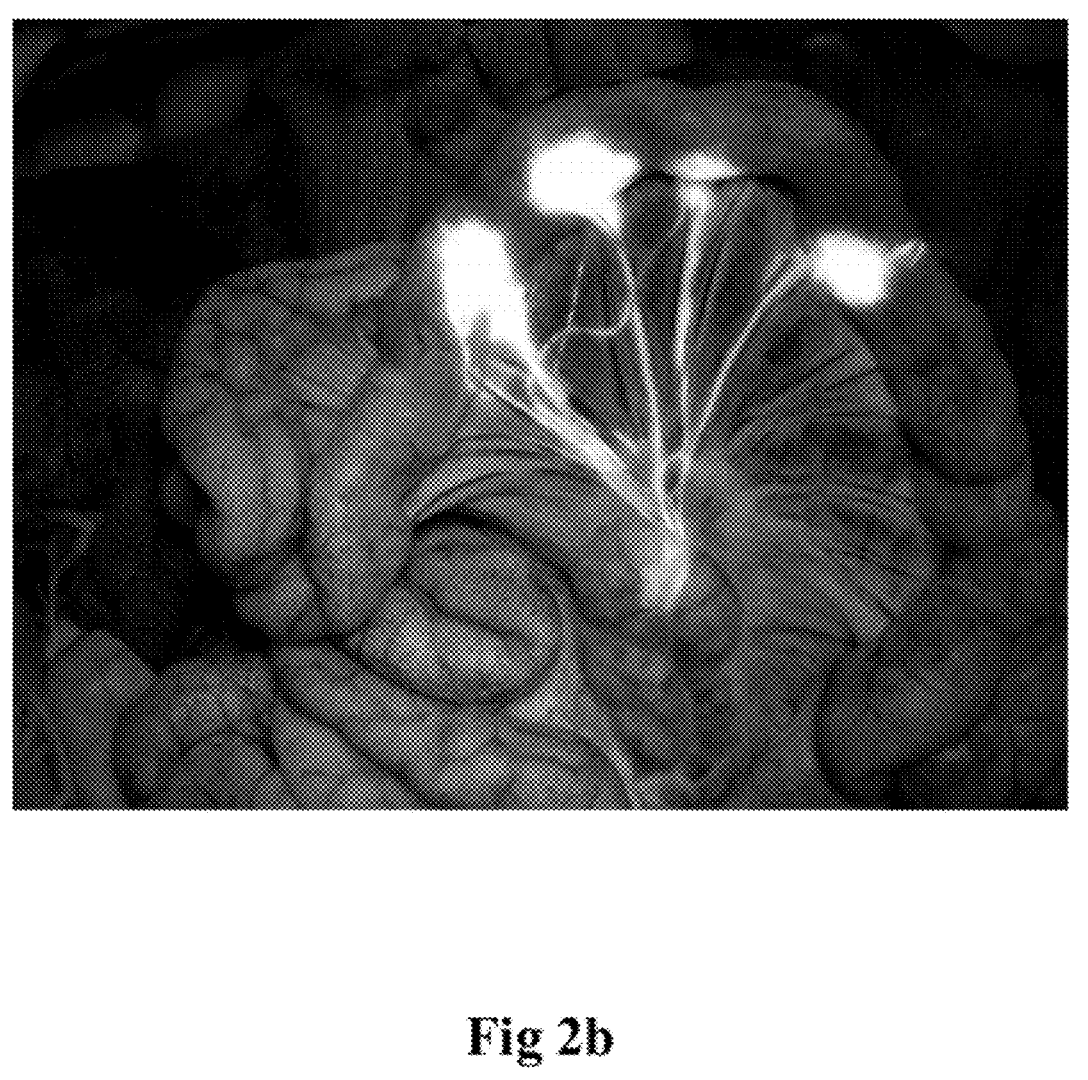

FIG. 2*b* illustrates the same surgical site as FIG. 2*a* but with polarization filters 4, 6 that are rotated relative to each other compared with FIG. 2*a*. Due to the rotation of the polarization filters 4, 6 against each other, the reflective parts of the excitation light are extinguished whereas the fluorescent zones are clearly delimitable.

The adjustment of the polarization filters 4, 6 occurs automatically without intervention of the surgeon, so that he can concentrate on the operation. For example, the evaluation unit 9 can automatically determine the image brightness from the output from the camera 2, and the evaluation unit 9 can automatically instruct the control unit 10 to adjust (for example, rotate) one or more of the filters 4, 6 until the brightness drops below a threshold value.

The capture parameters of the camera 2, e.g., the aperture, the white balance, the sensitivity, etc., are different due to the different brightnesses and different spectra when lighting with white light and with fluorescent lighting. The parameters of the camera 2 can be stored and they can be recalled according to the used lighting. Thereby the image reproduction can be improved or optimized.

Modifications of the depicted embodiment are possible. The number of the polarization filters is not limited to two. For example, only one polarization filter at the side of the camera 2 may be provided. In that case, irradiation occurs with nonpolarized light, which can be sufficient for certain uses.

The interference filter can be omitted or multiple wavelength filters can be provided.

As another example, the camera 2 can be carried out as a HDTV camera or any other camera.

According to a further modification, during evaluation, the distribution of brightness instead of the integral of the image brightness may be determined.

Other implementations are within the scope of the following claims.

What is claimed is:

1. A surgical lamp comprising:

a light source;

a camera;

at least one first polarization filter that is rotatable, the at least one first polarization filter to receive excitation light that is reflected from a surgical site and non-polarized light caused by fluorescence by the excitation light at the surgical site;

a filter positioned in front of a light entrance of the camera and configured to allow light having a defined wavelength range to pass through the filter, the defined wavelength range including wavelengths of the excitation light and the fluorescence light;

an electronic evaluation unit connected to the camera, the electronic evaluation unit being configured to evaluate the image brightness of an image captured by the camera; and a control unit connected to the at least one first polarization filter and to the electronic evaluation unit, the control unit being configured to rotate the at least one first polarization filter based on an evaluation by the electronic evaluation unit of the image captured by the camera.

2. The surgical lamp of claim 1, further comprising at least one second polarization filter such that a polarizer and an analyzer are formed from, respectively, the at least one second polarization filter and the at least one first polarization filter.

3. The surgical lamp of claim 2, wherein the at least one second polarization filter is rotatable.

4. The surgical lamp of claim 1, wherein the light source emits narrowband light.

5. The surgical lamp of claim 1, further comprising a mechatronic drive unit for rotating the at least one first polarization filter.

6. The surgical lamp of claim 1, wherein the at least one first polarization filter is placed between the camera and the surgical site.

7. The surgical lamp of claim 6, further comprising at least one second polarization filter that is placed between the light source and the surgical site.

8. The surgical lamp of claim 1, wherein the electronic evaluation unit is configured to determine the distribution of brightness in the whole region of the image.

9. A method for illuminating a surgical site with a surgical lamp including a light source, a camera, and at least one rotatable polarization filter, the method comprising:

applying a fluorophor to the surgical site;

illuminating the surgical site with excitation light for generating fluorescence radiation;

using a filter positioned in front of a light entrance of the camera and configured to allow light having a defined wavelength range to pass through the filter, the defined wavelength range including wavelengths of the excitation light and the fluorescence radiation;

capturing an image of polarized reflected excitation light and non-polarized fluorescence light of the surgical site with the at least one rotatable polarization filter and the camera;

evaluating an image brightness of the captured image; and rotating the at least one polarization filter based on the evaluation of the image captured by the camera, wherein the at least one polarization filter receives the excitation light that is reflected from the surgical site and the non-polarized light caused by fluorescence by the excitation light at the surgical site.

10. The method of claim 9, wherein the rotation occurs automatically.

11. The method of claim 9, wherein the excitation light is polarized light from the light source.

12. The method of claim 9, wherein the excitation light is narrowband light.

13. The method of claim 9, wherein rotating the at least one polarization filter includes rotating the at least one polarization filter automatically until the total brightness of a viewed zone in the captured image drops below a threshold value.

14. The method of claim 9, wherein rotating the at least one polarization filter includes rotating the at least one polarization filter until the area of brighter illuminated zones in the captured image drops below a threshold value.

15. The method of claim 9, wherein capturing the image includes placing the at least one polarization filter between the camera and the surgical site.

16. The method of claim 9, further comprising directing light from the light source through at least one second polarization filter that is placed between the light source and the surgical site.

17. A surgical lamp comprising:

a light source emitting excitation light;

a camera;

at least one first polarization filter that is rotatable and placed between a surgical site and the camera, the at least one first polarization filter receiving polarized excitation light from the light source that is reflected from the surgical site and non-polarized light that is caused by fluorescence by the excitation light at the surgical site;

at least one second polarization filter placed between the light source and the surgical site, the at least one second polarization filter polarizing light from the light source;

an electronic evaluation unit connected to the camera and configured to evaluate the image brightness of the image captured by the camera; and a control unit coupled to the at least one first polarization filter and to the electronic evaluation unit, the control unit being configured to rotate the at least one first polarization filter to reduce the image brightness.

* * * * *

UNITED STATES PATENT AND TRADEMARK OFFICE

CERTIFICATE OF CORRECTION

PATENT NO. : 8,294,081 B2
APPLICATION NO. : 12/269478
DATED : October 23, 2012
INVENTOR(S) : Rouven Rosenheimer et al.

It is certified that error appears in the above-identified patent and that said Letters Patent is hereby corrected as shown below:

In the Claims:

Column 5, line 38 (Claim 9, line 38), delete “fluorophor” and insert --fluorophore--.

Signed and Sealed this
Fourteenth Day of May, 2013

Teresa Stanek Rea
*Acting Director of the United States Patent and Trademark Office*